US005686619A

United States Patent [19]
Bay et al.

[11] Patent Number: 5,686,619
[45] Date of Patent: Nov. 11, 1997

[54] CHLOROALKYL PYRIDINIUM HYDROCHLORIDE COMPOUNDS AND PROCESSES FOR THEIR PREPARATION

[75] Inventors: William Elliott Bay; Matthew A. Brown; David R. Kilanowski, all of Fairfield, Conn.

[73] Assignee: Cytec Technology Corp., Wilmington, Del.

[21] Appl. No.: 399,302

[22] Filed: Mar. 6, 1995

Related U.S. Application Data

[62] Division of Ser. No. 247,179, May 20, 1994, Pat. No. 5,521,316.
[51] Int. Cl.[6] .................................................. C07D 213/61
[52] U.S. Cl. .......................... 546/339; 546/340; 546/346
[58] Field of Search .................................. 546/339, 340, 546/346

[56] References Cited

U.S. PATENT DOCUMENTS

| | | | |
|---|---|---|---|
| 2,520,037 | 8/1950 | Cohen | 546/344 |
| 3,412,095 | 11/1968 | Clark | 546/346 |
| 3,673,198 | 6/1972 | Doyle et al. | 546/342 |
| 3,699,227 | 10/1972 | Doyle et al. | 514/354 |
| 3,875,170 | 4/1975 | Matsumoto et al. | 546/187 |
| 4,429,132 | 1/1984 | Whittaker | 546/346 |
| 4,564,681 | 1/1986 | Marinak et al. | 546/345 |
| 4,778,896 | 10/1988 | Gallenkamp | 546/304 |
| 5,241,086 | 8/1993 | Mas et al. | 549/428 |
| 5,247,093 | 9/1993 | Tommey | 546/345 |

FOREIGN PATENT DOCUMENTS

| | | |
|---|---|---|
| A0373 464 | 6/1990 | European Pat. Off. . |
| 3-271290 | 12/1991 | Japan . |

OTHER PUBLICATIONS

Brewster, Ray Q., Organic Chemistry, third edition, p. 113, 1962.
Introduction to Organic Laboratory Techniques, A Contemporary Approach, second edition, by Donald L. Pavia, p. 481, 1982.
Mosher, Harry S. et al., Journal of American Chemical Society, 73 Oct.(1951) pp. 4925–4927.
Acosta, C. Kirk et al. J. Chem. Res., Synop. (5), (1991) pp. 110–111.
Vejdelek, Zdenek J. et al. in Collection Czechoslov. Chem. Communs. 16, (1951) pp.344–347.
Functionalized Dithia(2,5)pyridinophanes as Vitamin $B_6$ Analogues. Synthesis, Properties, and Catalytica Activity for Racemization Reaction, Masaaki Iwata et al., Riken (The Institute of Pysical and Chemica Research), Wako, Saitama 351-01, Bull Chem. Soc. Jpn.,(1985) vol. 58. No. 9 pp. 2502–2514 at 2508.
J. Med. Chem., vol. 24, 1981, pp. 1149–1155, Tanouchi et al. "Highly selective Inhibitors of Thromboxane Synthetase". Chemical Abstracts, vol. 17, 8068e, 1951 (sec AT from Vejdelek).
Org. Prep. Proced. Int. 24 (2) (1992)pp. 143–146 at 145.
Synthesis of Heterocyclic Analogs of a–Methyldopa, Tilley et al., Chemical Research Dept., Hormann–La Roche, Inc. (1979)pp. 333–337, J. Heterocyclic Ehcm. vol. 16.
[3H]Imidacloprid: Synthesis of a Candidate Radioligand for the Nicotinic Acetylcholine Receptor, Latli et al., Journal of Labelled Compounds and Radiopharmaceuticals–vol. XXXI, No. 8 (1992)pp. 609–613 at 611.

Primary Examiner—C. Warren Ivy
Assistant Examiner—D. Margaret M. Mach
Attorney, Agent, or Firm—Claire M. Schultz

[57] ABSTRACT

Provided is a process for preparing chloroalkyl pyridinium hydrochloride compounds and various regioisomers and analogs thereof having substantially high purity levels and yields and a free-flowing, non-dusting form.

23 Claims, No Drawings

CHLOROALKYL PYRIDINIUM HYDROCHLORIDE COMPOUNDS AND PROCESSES FOR THEIR PREPARATION

This is a divisional of application Ser. No. 08/247,179 filed on May 20, 1994, now U.S. Pat. No. 5,521,316.

This invention relates to highly pure chloroalkyl pyridinium hydrochloride compounds and processes for their preparation.

BACKGROUND OF THE INVENTION

Chloroalkyl pyridinium hydrochloride compounds, and particularly chloromethyl pyridinium hydrochloride compounds, also called picolyl chloride hydrochloride compounds, are generally used in the preparation of various pharmaceuticals, dyes, agricultural products and particularly as pharmaceutical intermediates. As such, chloroalkyl pyridinium hydrochloride compounds having significant impurity levels are very undesirable and oftentimes not tolerated in the end product for which it is used. It is therefore advantageous to use a chloroalkyl pyridinium hydrochloride compound in its most pure form.

In addition to purity, it is also beneficial if the morphology of the chloroalkyl pyridinium hydrochloride compound is one which is easy to handle from a processability standpoint. Current chloroalkyl pyridinium hydrochloride compounds, particularly 3-chloromethyl pyridinium hydrochloride, are available as solid powders that tend to clump and/or create dust problems and are difficult to contain. For those reasons they can pose processing, safety and/or environmental problems, particularly since some chloroalkyl pyridinium hydrochloride compounds are reported to be carcinogenic.

Despite the desire for relatively pure chloroalkyl pyridinium hydrochloride compounds that facilitate efficient processibility, the known methods for producing chloroalkyl pyridinium hydrochloride compounds, and particularly chloromethyl pyridinium hydrochloride, fail to provide such compounds.

In Mosher, Harry S. et al., Journal Of American Chemical Society, 73 October (1951) pp. 4925–4927, 3-chloromethyl and 4-chloromethyl pyridinium hydrochloride was prepared by first reducing ethyl nicotinate and ethyl isonicotinate with lithium aluminum hydride in anhydrous ether to produce 3-hydroxymethyl pyridine and 4-hydroxymethyl pyridine respectively. The resulting liquid 3-hydroxymethyl pyridine was separated from the distillate by converting to the hydrochloride. The 3- and 4-hydroxymethyl pyridine hydrochloride were added to a substantial excess amount of thionyl chloride and then refluxed followed by the addition of benzene to precipitate out the 3- and 4-chloromethyl Pyridine hydrochloride, respectively. Although the resulting 3-chloromethyl pyridine hydrochloride compound appears to be very pure, it apparently exists as a fluffy dusty powder which is difficult to process on a large scale basis.

Vejdelek, Zdenek J. et al. in Collection Czechoslov. Chem. Communs. 16, (1951) pp.344–7, discloses the preparation of 3-chloromethyl pyridinium hydrochloride from 3-hydroxymethyl pyridine and thionyl chloride in chloroform.

Japanese patent no. 3-271290 discloses the chlorination of 2-[4-(3-hydroxymethyl-2-pyridyl)oxyphenyl]propionic acid by thionyl chloride in benzene to give 2-[4-[3-(chloromethyl)-2-pyridyl]oxyphenyl]propionic acid.

Acosta, C. Kirk et al. J. Chem. Res., Synop. (5), (1991) pp. 110–11 discloses processes for synthesizing various unnatural amino acids. In the disclosed method of synthesis, 3-hydroxymethylquinoline is reacted with hydrogen chloride and thionyl chloride to produce reportedly good yields of 3-chloroalkylquinoline. No solvent is used and there is no description as to reactant amounts and the purity of the resulting 3-chloroalkylquinoline.

In Org. Prep. Proced. Int. 24 (2) (1992) pp. 143–146, 5-bromo-3-hydroxymethylpyridine was reacted with hydrogen chloride in diethyl ether. The resulting precipitate was collected by vacuum filtration and then dissolved in thionyl chloride and refluxed. Diethyl ether was used to precipite the 5-bromo-3-chloromethylpyridinium hydrochloride product. Since the product produced was reportedly off white in color this method apparently does not provide a highly pure product.

While it is known to use thionyl chloride to produce chloroalkyl pyridinium hydrochloride, it appears that the known procedures either generate high levels of impurities and/or produce a solid product that has handling problems, e.g., dusting, clumping. Moreover, many of the known procedures produce low yields or are very difficult to perform on a large scale. In view of these shortcomings, there exists a need for an improved process for producing chloroalkyl pyridinum hydrochloride compounds and especially a process for preparing very pure chloroalkyl pyridinium hydrochloride compounds in a form that is easy to process.

The inventors of the instant invention have surprisingly discovered a process for preparing highly pure, i.e., at least about 97 weight percent pure, chloroalkyl pyridinium hydrochloride compounds, including analogs and regioisomers thereof, in a substantially non-dusting, free-flowing form which has processing advantages.

In the processes of the instant invention, thionyl chloride is admixed with a solution or dispersion of a hydroxyalkyl pyridinium hydrochloride compound in a liquid component which is a non-solvent for the chloroalkyl pyridinium hydrochloride product. Preferably, the solution or dispersion of hydroxyalkyl pyridinium hydrochloride is prepared by reacting a minimum amount of hydrogen chloride or hydrochloric acid with a hydroxyalkyl pyridine compound in a liquid hydrocarbon, preferably an aromatic hydrocarbon such as toluene. The hydroxyalkyl pyridinium hydrochloride in the solution or dispersion reacts with thionyl chloride to form the chloroalkyl pyridinium hydrochloride, a portion of which spontaneously forms as a solid or crystallizes in the reaction mixture. Highly pure, dust-free, free-flowing powders of chloroalkyl pyridinium hydrochloride, including 3-chloromethyl pyridinium hydrochloride, can be recovered from the reaction mixture in high yields on the order of at least about 97 percent, based on the molar equivalents of hydroxyalkyl heterocyclic aromatic compounds (usually the equivalents of hydroxyalkyl pyridine), preferably at least about 99 percent, same basis.

SUMMARY OF THE INVENTION

The present invention provides a process for the preparation of chloroalkyl pyridinium hydrochloride compounds comprising the steps of:
 a) generating a solution or a dispersion comprising a hydroxyalkyl pyridinium hydrochloride compound in a medium comprising at least one non-solvent for the chloroalkyl pyridinium hydrochloride compound;
 b) admixing thionyl chloride with said solution or dispersion generated in step (a) to form a reaction mixture;
 c) reacting the thionyl chloride with the hydroxyalkyl pyridinium hydrochloride to form the chloroalkyl pyridinium hydrochloride, at least a portion of which forms as a solid in the reaction mixture.

It is generally preferred that the hydroxyalkyl pyridinium hydrochloride compound has the general formula:

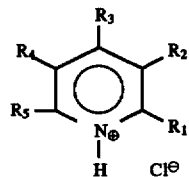

wherein

R$_1$ through R$_5$ are substituents independently selected from the group consisting of:

hydrogen, halogen, a hydrocarbyl group having 1 to 30 carbons, a halo substituted hydrocarbyl group having 1 to 30 carbons and any two of R$_1$ through R$_5$ together form a ring selected from the group consisting of aromatic, cycloalkane, and heterocyclic rings; provided that at least one of R$_1$ through R$_5$ is a hydroxyalkyl group.

The solution or dispersion in step (a) may be generated by reacting a hydroxyalkyl pyridine compound with at least about 0.25 equivalents, more preferably at least about 1.0 equivalent, of hydrogen chloride and/or hydrochloric acid, based on the number of basic heteroaromatic equivalents, in a medium comprising at least one non-solvent for the chloroalkyl pyridinium hydrochloride.

Also included in the present invention is a process for the preparation of 3-chloromethyl pyridinium hydrochloride which comprises the steps of:

a) generating a solution or a dispersion comprising 3-hydroxymethyl pyridinium hydrochloride in a medium comprising a non-solvent for 3-chloromethyl pyridinium hydrochloride;

b) admixing thionyl chloride with said solution or dispersion generated in step (a) to generate a reaction mixture; and c) reacting thionyl chloride with 3-hydroxymethyl pyridinium hydrochloride to form 3-chloromethyl pyridinium hydrochloride, at least a portion of which forms as a solid in the reaction mixture.

Preferably, the solution or dispersion in step (a) is generated by reacting 3-hydroxymethyl pyridine with at least about 0.25 equivalents of hydrogen chloride or hydrochloric acid, based on the number of pyridine nitrogen equivalents, preferably at least about 1.0 equivalent, same basis, in a medium comprising at least one non-solvent for 3-chloromethyl pyridinium hydrochloride. Preferably, the non-solvent is toulene or a mixture of toulene and a hydrocarbon.

In yet another embodiment of the present invention, substantially pure, substantially non-dusting 3-chloromethyl pyridinium hydrochloride is prepared by a process comprising the steps of:

a) generating a solution or dispersion comprising 3-hydroxymethyl pyridinium hydrochloride in a medium comprising toluene, by reacting in said medium, 3-hydroxymethyl pyridine with at least about 1 equivalent of hydrogen chloride, based on the number of pyridine nitrogen equivalents;

b) admixing thionyl chloride with said solution or dispersion generated in step (a) to form a reaction mixture;

c) heating the reaction mixture to a temperature ranging from about 75° C. to about 90° C. for a period of time ranging from about 0.5 to about 10 hours;

d) heating the reaction mixture to a second temperature ranging from about 90° C. to about 100° C. and maintaining said second temperature within said range for a period of time of from about 3 minutes to about 6 hours; and e) recovering 3-chloromethyl pyridinium hydrochloride from the reaction mixture in a substantially high yield.

The processes of the present invention provide many advantages over those in the prior art including, for example: (1) the processes of the instant invention produce chloroalkyl pyridinium hydrochloride compounds having higher levels of purity than chloroalkyl pyridinium hydrochloride compounds currently available; (2) the processes of the instant invention produce chloroalkyl pyridinium hydrochloride compounds in a free-flowing, non-dusting form which has processibility advantages; (3) the processes described herein produce a white product which is preferred in some end uses such as pharmaceuticals; (4) the processes described herein may be implemented on a large scale more easily than some of the prior art processes; and (6) the processes described herein produce chloroalkyl pyridinium hydrochloride in substantially high yields.

The present invention also provides substantially pure, substantially non-dusting compositions of matter comprising chloroalkyl pyridinium hydrochloride having the general formula:

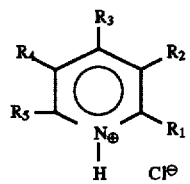

wherein R$_1$ through R$_5$ are substituents independently selected from the group consisting of:

hydrogen, halogen, a hydrocarbyl group having 1 to 30 carbons, a halo substituted hydrocarbyl group having 1 to 30 carbons and any two of R$_1$ through R$_5$ together form a ring selected from the group consisting of aromatic, cycloalkane, and heterocyclic rings; provided that at least one of R$_1$ through R$_5$ is a chloroalkyl group. A preferred embodiment of this invention provides for substantially pure, substantially non-dusting composition of matter comprising 3-chloromethyl pyridinium hydrochloride.

Preferably, the compositions of matter described herein are white, free-flowing powders and have a particle size distribution such that at least 75 weight percent of the particles have a diameter greater than 300 microns.

DETAILED DESCRIPTION OF THE PREFERRED EMBODIMENTS

The present invention generally provides a process for preparing chloroalkyl pyridinium hydrochloride compounds from thionyl chloride and a hydroxyalkyl pyridinium hydrochloride compound having the formula:

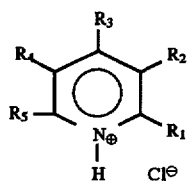

wherein $R_1$ through $R_5$ are substituents independently selected from the group consisting of: hydrogen, halogen, a hydrocarbyl group having 1 to 30 carbons, a halo substituted hydrocarbyl group having 1 to 30 carbons and any two substituents together form a ring selected from the group consisting of aromatic, cycloalkane, and heterocyclic rings; provided that at least one of $R_1$ through $R_5$ is a hydroxyalkyl group. The hydroxyalkyl group generally can have about 1 to 30 carbons, preferably about 1 to 15 carbons and most preferably about 1 to 4 carbons. The phrases "hydrocarbyl group" and "halo substituted hydrocarbyl group" usually include substituents comprising carbon and hydrogen such as alkyl groups, haloalkyl groups, cycloalkyl groups, arylcycloalkyl groups, halo substituted cycloalkyl groups, halo substituted arylcycloalkyl groups, aryl groups, halo substituted aryl groups hetercyclic rings and halo substituted heterocyclic rings. Generally the alkyl groups described herein contain 1 to 30 carbons, usually about 1 to about 20 carbons, preferably about 1 to about 10 carbons and more preferably about 1 to about 4 carbons, with 1 carbon being most preferred.

Generally, $R_1$ through $R_5$ substituents and substituent combinations on the hydroxyalkyl pyridinium hydrochloride ring are those that do not interfere with the chlorination of that pyridinium compound in its reaction with thionyl chloride. The various types of hydrocarbyl groups, halogens, halo substituted groups and ring substituents suitable and preferable for the present invention is known or can be readily determined by one of ordinary skill in the art. For example, when any $R_1$ through $R_5$ is a haloalkyl substituent, chloroalkyl or fluoroalkyl groups are preferred. When any of $R_1$ through $R_5$ are aromatic rings phenyl and naphthyl groups are preferred. When any of $R_1$ through $R_5$ groups together form a cycloalkane ring, groups such as cyclohexane and cyclopentane are preferred.

It is more preferred to use various regioisomers of hydroxyalkyl pyridinium hydrochloride such that $R_1$ through $R_5$ are hydrogen provided that at least one of $R_1$ $R_2$, $R_4$, or $R_5$, preferably one, is a hydroxymethyl group. It is most preferred to use 3-hydroxyalkyl pyridinium hydrochloride, most preferably 3-hydroxymethyl pyridinium hydrochloride. Representative examples of preferred hydroxyalkyl pyridinium hydrochloride compounds used in the instant invention include analogs of the following hydrochloride salts: analogs of 2-hydroxyalkyl pyridinium hydrochloride such as 4-methyl-2-hydroxyalkyl pyridinium; 5-methyl- 2-hydroxyalkyl pyridinium; 6-methyl-2-hydroxyalkyl pyridinium and 5-phenyl-2-hydroxyalkylpyridinium; 4-propyl, 5-fiuoromethyl-2-hydroxyalkyl pyridinium; analogs of 3-hydroxyalkyl pyridinium hydrochloride such as 4-methyl-3-hydroxyalkyl pyridinium; 5-methyl-3-hydroxyalkyl pyridinium; 6-methyl-3-hydroxyalkyl pyridinium; 4-butyl-3-hydroxyalkyl pyridinium; 5-phenyl-3-hydroxyalkyl pyridinium; 6-phenyl-3-hydroxyalkyl pyridinium; 5-chloroalkyl-3-hydroxyalkyl pyridinium and 6-chloroalkyl-3-hydroxyalkyl pyridinium; analogs of 4-hydroxyalkyl pyridinium hydrochloride such as 2-ethyl-4-hydroxyalkyl pyridinium; 6-methyl-4-hydroxyalkyl pyridinium; 2-phenyl-4-hydroxyalkyl pyridinium; 6-phenyl-4-hydroxyalkyl pyridinium; analogs of 5-hydroxyalkyl pyridinium hydrochloride such as 2-methyl-5-hydroxyalkyl pyridinium; 3-propyl-5-hydroxyalkyl pyridinium and 3-phyenyl-5-hydroxyalkyl pyridinuim; and analogs of 6-hydroxyalkyl pyridinium hydrochloride such as 3-methyl-6-hydroxyalkyl pyridinuim; 4-ethyl-6-hydroxymethyl pryidinuim; 3-tolyl-6-hydroxymethyl pyridinuim.

The various hydroxyalkyl pyridinium hydrochloride analogs and regioisomers contemplated within this invention are generally referred top herein as the "hydroxyalkyl pyridinium hydrochloride" compounds. The hydroxyalkyl pyridinium hydrochloride compounds used in the process of the present invention are preferably in a medium comprising at least one non-solvent for the chloroalkyl pyridinium hydrochloride product, generally referred to herein as non-solvent. As such, the hydroxyalkyl pyridinium hydrochloride compounds form a solution or dispersion with the liquid medium. The term "dispersion" herein broadly includes emulsions and suspensions and the phrase "solution or dispersion" refers to the medium which comprises the hydroxyalkyl pyridinium hydrochloride and at least one non-solvent. The amount of hydroxyalkyl pyridinium hydrochloride present in the dispersion or solution is not critical and may generally range from about 0.5 to about 2 gram molar equivalents, preferably from about 1 to about 1.5 gram equivalents per pound of non-solvent. Preferably, the dispersion has a uniform consistency with little clumping. The solution or dispersion of hydroxyalkyl pyridinium hydrochloride may preferably contain, in addition to the non-solvent, hydroxyalkyl pyridine.

To generate a solution or dispersion comprising a hydroxyalkyl pyridinium hydrochloride compound in a medium comprising at least one non-solvent as described above, it is preferred to react a hydroxyalkyl pyridine compound with hydrogen chloride and/or hydrochloric acid, preferably in the presence of a medium comprising at least one non-solvent for chloroalkyl pyridinium hydrochloride. Suitable hydroxyalkyl pyridine compounds are those having the formula:

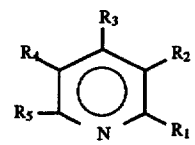

wherein $R_1$ through $R_5$ are substituents independently selected from the group consisting of: hydrogen, halogen, a hydrocarbyl group having 1 to 30 carbons, a halo substituted hydrocarbyl group having 1 to 30 carbons; and any two substituents together form a ring selected from the group consisting of aromatic, cycloalkane, and heterocyclic rings; provided that at least one of $R_1$ through $R_5$ is a hydroxyalkyl group.

Typical $R_1$ through $R_5$ substituents on the hydroxyalkyl pyridine ring are groups that do not interfere with the conversion of the hydroxyalkyl pyridine to its hydrochloride and do not interfere with the chlorination of the hydroxyalkyl pyridine and pyridinium hydrochloride. Suitable hydroxyalkyl pyridine compounds generally include those having the same substituents as the hydroxyalkyl pyridinium hydrochloride compounds described above. Preferred hydroxyalkyl pyridine compounds used in the process of the instant invention may be readily ascertained by one skilled in the art; more preferred pyridine compounds include various regioisomers of hydroxyalky pyridine, preferably hydroxymethyl pyridine, such that $R_1$ through $R_5$ are hydrogen provided that one of $R_1$ through $R_5$ is a hydroxyalkyl group. 3-hydroxymethyl pyridine is most preferred.

The various hydroxyalkyl pyridine analogs and regioisomers described above are generally referred to herein as the "hydroxyalkyl pyridine" compounds while various analogs and regioisomers of the chloroalkyl pyridinium hydrochloride products are generally referred to herein as "chloroalkyl pyridinium hydrochloride" compounds or "product" or both.

While anhydrous conditions are not required for preparing the solutions or dispersions used in the instant invention, they are preferred. It is also more preferred to use hydrogen chloride than hydrochloric acid to prepare solutions or dispersions of hydroxyalkyl pyridinium hydrochloride in a medium, which is generally liquid. The medium comprises at least one non-solvent, which is preferably non-reactive under reaction conditions and may include other substances which do not react with the reactants under reaction conditions. Unreacted reactants may also be included in the liquid medium.

The term non-solvent herein refers to a liquid, preferably a hydrocarbon, in which the chloroalkyl pyridinium hydrochloride product is substantially insoluble. Preferably not more than about 1 gram, more preferably 0.5 grams, of the chloroalkyl pyridinium hydrochloride is soluble per liter of non-solvent at ambient conditions. Suitable and preferable non-solvents may vary, depending on the particular chloroalkyl pyridinium hydrochloride desired. Generally, preferred non-solvents will produce, according to the process of the instant invention, chloroalkyl pyridinium hydrochloride in substantially non-dusting form. It may, in some instances, be preferred that the non-solvent is also one in which the hydroxyalkyl pyridine is substantially soluble. More preferably, the non-solvents used in the instant invention include aromatics, long chain aliphatic hydrocarbons having 6 or more carbons, preferably 8 or more carbons and cycloaliphatic hydrocarbons. Suitable non-solvents include but are not limited to methylcyclohexane, mesitylenes, benzene, xylenes, octanes, heptanes, hexane, cyclohexane, mixtures thereof and the like. Generally aromatic, cycloalkane and cycloalkene hydrocarbons are preferred non-solvents and it is most preferred to use toluene or mixtures of toluene and one or more hydrocarbons such as but not limited to methylcyclohexane or cyclohexane and the like in proportions of about 2:3 toluene to hydrocarbon to about 9:1. The amount of non-solvent used is generally a quantity that renders the solution or dispersion mixable by stirring.

The reaction product of the hydroxyalkyl pyridine compound with hydrogen chloride and/or hydrochloric acid (collectively referred to herein as "HCl") is the resulting hydroxyalkyl pyridinium hydrochloride and any unreacted hydroxymethyl pyridine that may be present, depending on the amount of HCl used. Whether the reaction product is contained within a solution or dispersion depends on the solubilities of hydroxyalkyl pyridine and hydroxyalkyl pyridinium hydrochloride in the non-solvent. For example, when 3-hydroxymethyl pyridine is reacted with HCl using toluene as a non-solvent, the resulting reaction product usually forms a dispersion with the toluene.

The amount of HCl used to prepare the solutions or dispersions of hydroxyalkyl pyridinium hydrochloride is at least about 0.25 equivalents, based on the number of basic heteroatomatic equivalents (usually the initial number of pyridine nitrogen equivalents), generally at least about 0.30 equivalents, preferably at least about 0.50 equivalent and more preferably at least about 1.0 equivalent of HCl, based on the number of pyridine nitrogen equivalent or, more generally, the number of basic heteroatoms. At least about 1.0 equivalent, more preferably a slight excess amount of HCl is needed to ultimately obtain a white chloroalkyl pyridinium hydrochloride product according to the process of the present invention.

It is desirous to add the HCl to the hydroxyalkyl pyridine in the non-solvent and this addition is usually conducted under agitation, preferably with a means for controlling heat evolution, particularly with large scale reactions, since the reaction of HCl with the hydroxyalkyl pyridine tends to be exothermic. The rate at which the HCl is added is not critical, though it may be varied to control the heat of evolution and the temperature of the resulting solution or dispersion to which thionyl chloride is added. It is more preferred to add HCl to the hydroxyalkyl pyridine and non-solvent over a period of time such that the heat of reaction is controllable, preferably such that the heat of reaction provides a temperature suitable for subsequent chlorination. When less than 1 equivalent of HCl is reacted with hydroxyalkyl pyridine to generate a solution or dispersion comprising hydroxyalkyl pyridinium hydrochloride, the resulting solution or dispersion also contains hydroxyalkyl pyridine. The molar equivalents of hydroxyalkyl pyridinium hydrochloride present in the solution or dispersion is at least about 25 percent, based on the total equivalents of hydroxyalkyl pyridinium hydrochloride and hydroxyalkyl pyridine in the solution or dispersion, generally at least about 30 percent to about 40 percent, same basis, preferably at least about 50 percent, same basis, and more preferably at least about 75 percent, same basis. It is most preferred that the solution or dispersion comprise at least about 100 percent molar equivalents of hydroxyalkyl pyridinium hydrochloride with no hydroxyalkyl pyridine.

Alternatively, though less preferably, the solution or dispersion may be prepared by reacting HCl and hydroxyalkyl pyridine outside the presence of the non-solvent, and then admixing the resulting reaction product with the non-solvent to form the solution or dispersion of hydroxyalkyl pyridinium hydrochloride. Or, other methods known in the art may be used, though these methods may be less preferred.

Prior to adding the thionyl chloride to the solution or dispersion of hydroxyalkyl pyridinium hydrochloride, it is preferred to maintain the temperature of the solution or dispersion to a temperature ranging from about 20° C. to about 100° C., more preferably to a temperature from about 70° C. to about 79° C. Since the reaction of hydroxyalkyl pyridine and HCl tends to be exothermic, the resulting solution or dispersion which contains the reaction product may be cooled to reach a temperature within this range. Prior to adding thionyl chloride to the solution or dispersion, it is generally desirous to maintain the temperature of the solution or dispersion to a temperature below the boiling point range of thionyl chloride, generally about 79° C., to avoid refluxing the thionyl chloride during the chlorination reaction.

The solution or dispersion of hydroxyalkyl pyridinum hydrochloride is admixed with thionyl chloride to form a reaction mixture. The quantity of thionyl chloride is generally an amount ranging from about 200 equivalent percent excess or less, based on the number of hydroxy equivalents of the hydroxyalkyl pyridinium hydrochloride and any hydroxyalkyl pyridine in the solution or dispersion (or the hydroxy equivalents of hydroxyalkyl pyridine initially reacted with the HCl). Preferably up to about 100 equivalent percent excess thionyl chloride may be used, more preferably up to about 10 equivalent percent excess thionyl chloride. It is also preferred to use at least about 1 equivalent, more preferably at least about 1 equivalent percent excess thionyl chloride based on the number of hydroxy equivalents of the hydroxyalkyl pyridinium hydrochloride and any hydroxyalkyl pyridine in the solution or dispersion. Thus, the preferred amount of thionyl chloride should range from 0 to about 10 equivalent percent excess, same basis, and most preferably a slight excess amount of about 1 to about 5 equivalent percent excess, same basis.

To obtain a white chloroalkyl pyridinium hydrochloride product, the amount of thionyl chloride used should be at least an equimolar amount based on the number of moles of the hydroxyalkyl pyridinium hydrochloride and any hydroxyalkyl pyridine in the solution or dispersion. It is also important to use a pure grade of thionyl chloride in order to produce a white chloroalkyl pyridinium hydrochloride product. The chlorination reaction appears to proceed at a faster rate when amounts of at least about 30 equivalent percent excess thionyl chloride are used.

Upon admixing the solution or dispersion of hydroxyalkyl pyridinium hydrochloride with thionyl chloride, the thionyl chloride is believed to react with the hydroxyalkyl pyridinium hydrochloride and any hydroxyalkyl pyridine which may be present in the reaction mixture. Though heating is not necessary, it is preferred to warm the reaction mixture during the addition of thionyl chloride, preferably to maintain the temperature of the reaction mixture to anywhere from about 70° C. to about 79° C. The temperatures provided herein are given assuming atmospheric pressure. The processes described herein may be performed under a variety of pressures; in these cases it would be well within the ability of those skilled in the art to adjust the temperatures cited herein accordingly. The thionyl chloride and hydroxyalkyl pyridinium hydrochloride are preferably reacted at a temperature that does not exceed the boiling point of the reaction mixture, which includes the medium comprising the non-solvents(s), the reactants and any unreacted reactants. Although a solvent which differs from the non-solvent may be used during chlorination, the non-solvent should remain in the reaction mixture. Generally, it is not necessary and less preferred to add an additional solvent for the chlorination reaction.

The addition of thionyl chloride is preferably done at a rate such that gas evolution is controlled. It is preferred to add thionyl chloride to the dispersion or solution comprising hydroxyalkyl pyridinium hydrochloride over a period of time ranging from about 15 minutes to about 20 hours while maintaining the temperature within a range of from about 20° C. to about 100° C. More preferably, one may add thionyl chloride to the dispersion or solution over a time ranging from about 20 minutes to about 3 hours while maintaining the temperature from about 70° C. to about 79° C. The aforesaid addition times may be extended as the volume of the reaction increases. The chlorination reaction should be conducted under anhydrous conditions, preferably under nitrogen. If hydrochloric acid had been used to prepare the hydroxyalkyl pyridinium hydrochloride, the solution or dispersion comprising such should be dried using methods known in the art prior to adding thionyl chloride. Since hydrogen chloride and sulfur dioxide gasses are emitted during the chlorination reaction, it is preferred to have a means for neutralizing and containing the gases such as caustic scrubbers or the like. It is also preferred to implement a means for capturing and recycling the hydrogen chloride gas for reuse in the preparation of the solution or dispersion comprising the hydroxyalkyl pyridinum hydrochloride.

It is also within the scope of the present invention to prepare the solution or dispersion of hydroxyalkyl pyridinium hydrochloride in the presence of thionyl chloride such that preparation of hydroxyalkyl pyridinium hydrochloride and chlorination of hydroxyalkyl pyridinium hydrochloride occurs in one step. Preferably, however, the solution or dispersion of hydroxyalkyl pyridinium hydrochloride is formed first and then the thionyl chloride is added to said solution or dispersion to produce chloroalkyl pyridinium hydrochloride.

Without wishing to be bound by any theory, there is believed to be an equilibrium between the reacting phase of the thionyl chloride with hydroxyalkyl pyridinium hydrochloride and the formation of the solid chloroalkyl pyridinium hydrochloride product. As the product crystallizes or forms as a solid, heat is released and there can be an explosive release of sulfur dioxide and HCl gas if a substantial amount of uncrystallized product rapidly crystallizes toward the end of the chlorination reaction. To avoid this, it is preferred to initiate crystallization at a somewhat low temperature, preferably after the thionyl chloride begins to react with the hydroxyalkyl pyridinium chloride, by heating, usually under agitation the reaction mixture to a temperature and for a period of time sufficient for at least a portion of the chloroalkyl pyridinium hydrochloride to spontaneously form as a solid in the reaction mixture. Generally, and particularly with respect to making 3-chloromethyl pyridinium hydrochloride using toluene as the non-solvent, one may heat the reaction mixture to a temperature ranging from about 75° C. to about 90° C., more preferably to a temperature from about 80° C. to about 85° C. and maintain said temperature within these ranges until a portion of the chloroalkyl pyridinium hydrochloride forms as a solid in the reaction mixture. The formation of solids broadly includes precipitation as well as crystallization. In performing this preferred step, the temperature is usually maintained for a period of time ranging from about 0.5 to about 10 hours, more preferably from about 1 to about 2 hours. To expedite the reaction, it is also preferred to heat the reaction mixture, after a portion of the chloroalkyl pyridinium hydrochloride forms as a solid in the reaction mixture, to a higher temperature which drives the reaction to completion, indicated by the termination of gas emissions. Preferably this temperature ranges from about 90° C. to about 100° C. for making 3-chloro methyl pyridinium hydrochloride in toluene; it is also preferred to maintain the temperature within that range until the evolution of gases stops, which is typically, for a period of time ranging from about 3 minutes to about 6 hours, more preferably from about 0.5 to about 2 hours. More preferably, the reaction mixture may be heated to a temperature ranging from about 93° C. to about 97° C. Ad the temperature maintained within this range for a period of time ranging from about 3 minutes to about 6 hours, more preferably from about 0.5 hours to about 2 hours. The final heating step tends to facilitate the release of sulfur dioxide and hydrogen chloride gas and drives the reaction to completion. This final heating is preferably conducted with agitation of the mixture, preferably after the reaction mixture has been heated and maintained to a temperature from about 75° C. to about 90° C. It is preferred, particularly with large scale reactions, that crystallization of the chloroalkyl pyridinium hydrochloride product not initially occur within a high temperature range (e.g., 90° C. to 100° C.) to avoid explosive release of sulfur dioxide as discussed above. It is preferred that crystallization occur at a lower temperature, preferably a temperature ranging from about 70° C. to about 90° C., more preferably from about 80° C. to about 85° C.

The preferred temperatures and time periods set forth herein have been found to operate particularly well in preparing 3-chloromethyl pyridinium hydrochloride using toluene as a non-solvent. The aforesaid preferred temperatures are believed to contribute to the desired non-dusting morphology of the product. As for the broader scope of the present invention, it is within the ability of those skilled in the art to adjust these temperatures and times to suit the non-solvent used and the particular chloroalkyl pyridinium hydrochloride desired. Crystallization of any chloroalkyl pyridinium hydrochloride may occur at ambient conditions, albeit at a slower rate. It is important that the crystallization or formation of solid product take place in the reaction mixture which comprises at least one non-solvent.

After formation of solid chloroalkyl pyridinium hydrochloride in the reaction mixture, the reaction mixture is preferably cooled to ambient temperature and the solid chloroalkyl pyridinium hydrochloride is recovered by methods known in the art such as, for example, filtration, centrifuging, or evaporation of volatile components. The solid chloroalkyl pyridinium hydrochloride product may be washed with any solvent that will dissolve thionyl chloride and not react with the chloroalkyl pyridinium hydrochloride product. Preferred washing solvents include but are not limited to the non-solvents described herein such as toluene, methylcyclohexane, hexanes, heptanes, octanes, xylenes, and mesitylenes as well as petroleum ethers. Solid product may be further dried by conventional means, preferably with a vacuum to remove trace amounts of solvent and thionyl chloride. Substantially high yields on the order of at least 97 weight percent may be recovered, based generally on the number of molar equivalents of hydroxyalkyl heterocyclic aromatic compounds present in the reaction mixture (preferably the molar equivalents of hydroxyalkyl pyridine), preferably at least about 98 weight percent, same basis, most preferably at least about 99 weight percent, same basis.

The chloroalkyl pyridinium hydrochloride compounds or compositions of matter of the present invention usually exist as free-flowing powders and, are also substantially non-dusting. Using light microscopy, the chloroalkyl pyridinuim hydrochloride compounds of the present invention appear to be pseudo cubic aggregates, generally crystalline aggregates which are substantially adhesive.

Preferably, the particle size distribution is such that a sufficient percentage of particles, herein aggregates, have an average diameter greater than 300 microns such that the material is substantially non-dusting. In other words, a small portion of the aggregates should be fine particles or 300 microns or less in size. Usually most of or at least about 20 weight percent of the aggregates have an average diameter greater than 300 microns as measured by microscopy, using automated image analysis. Preferably at least about 50 weight percent have an average diameter greater than 300 microns, more preferably at least about 75 weight percent of the aggregates have an average diameter greater than 300 microns. And it is most preferred that the chloroalkyl pyridinum hydrochloride powders of the present invention have at least about 90 weight percent, oftentimes at least 95 weight percent of its aggregates greater than 300 microns in size, on average. It is noted that methods of determining particle size distribution such as mechanical selves, and the like may provide inaccurate measurements due to consequential breaking of the psuedo-cubic aggregates. As a result of all of the physical characteristics described above, the compounds of the present invention provide many advantages with respect to processing and handling.

Though the invention is not to be limited or bound to any theory described herein, it is believed that the high purity levels of chloroalkyl pyridinium hydrochloride produced by the processes described herein are achieved, at least in part, as a result of the presence of some hydroxyalkyl pyridinium hydrochloride in the solution or dispersion. In reacting thionyl chloride with the hydroxyalkyl pyridinium hydrochloride, impurity formation is inhibited, or at least significantly reduced, since the nitrogen in the hydroxyalkyl pyridinium hydrochloride is retarded from reacting with chloroyalkyl groups to form impurities. Similarly, the reaction between chloroalkyl pyridinium hydrochloride and chloroalkyl groups to form impurities is significantly reduced. It has been found that this impurity inhibition continues during chlorination inasmuch as the hydrogen chloride produced as a byproduct of that reaction tends to react with any unprotonated pyridine compound in the reaction mixture, converting it to its hydrochloride form and thus rendering it less available to form impurities.

The resulting chloroalkyl pyridinium hydrochloride products of this invention are substantially pure. Generally, they have a purity of at least about 97 weight percent, more preferably at least about 98 weight percent and most preferably at least about 99 weight percent. The purity values described herein are determined according to a titrimetric assay which differentiates the product from impurities. This titrimetric method has an approximate error of about 1 to about 2% (about 80% to about 90% of measurements should fall within this range of error). Generally, to determine the purity of chloroalkyl pyridinium hydrochloride compounds described herein, a sample of the product is dissolved in 5 parts water and 100 parts acetone, preferably first dissolving the sample in the water and then adding the acetone to prepare a solution of product. This solution of product is titrated potentiometrically with about a 0.1N solution of tetrabutylammonium hydroxide in 2-propanol using a Metrohom E636 Titroprocessor.

Compositions of matter comprising chloroalkyl pyridinium hydrochloride made in accordance with preferred processes disclosed herein are not only substantially pure but can also be white in color. The chloroalkyl pyridinium hydrochloride compounds described herein are hygroscopic and if exposed to moisture may tend to hydrolyze. Over time, the compounds of the instant invention may decompose to generate heat and hydrogen chloride gas and therefore are preferably stored at cool temperatures in the range of 0° to 25° C. before being used.

It is believed that one skilled in the art can use the preceding description to utilize the present invention to its fullest extent.

DESCRIPTION OF THE PREFERRED EMBODIMENTS

The following examples are set forth for illustration purposes only and are not to be construed as limitations on the present invention, as set forth in the appended claims. Parts as described herein are based upon weight of components unless designated otherwise.

The purity values set forth in the examples were determined using the titrametric assay method described above.

EXAMPLE 1

A dry, six neck glass reaction vessel of a Mettier RC1 reaction calorimeter was set up with an overhead stirrer, reflux condenser, 2 inlet tubes, heat calibration probe, and temperature sensor. The exit of the condenser was connected to a nitrogen bubbler which vented into a caustic scrubber. The reaction setup was flushed with dry nitrogen. The following reaction was carried out under an atmosphere of dry nitrogen. The reaction flask was charged with one part 3-hydroxymethyl pyridine and 3.47 parts toluene. A cylinder of anhydrous hydrogen chloride was equipped with a pressure regulator. The pressure regulator was connected with a piece of flexible hose to a short piece of glass tubing. The glass tube was placed through the rubber septum on the reaction flask so that its opening was just above the surface of the reaction mixture. Hydrogen chloride was blown onto the surface of the stirred reaction mixture until 0.33 parts hydrogen chloride had been absorbed by the reaction mixture. A thick, white precipitate formed during the addition of the hydrogen chloride. This addition was exothermic and the reaction mixture temperature was allowed to rise to 70° C. The rubber septum and glass tube were removed from the reaction flask. About 1.11 parts thionyl chloride was added to the stirred reaction mixture using a dispensing pump. The temperature of the reaction mixture was maintained between 70° and 75° C. during the thionyl chloride addition. Hydrogen chloride and sulfur dioxide evolved from the reaction mixture during the thionyl chloride addition. The solids in the reaction mixture settled into a thick paste at the bottom of the reaction flask during the first quarter to one third of the thionyl chloride addition. Gradually this paste liquified as the thionyl chloride addition was continued. The reaction mixture was a stirred suspension of two immiscible liquid phases at the end of the thionyl chloride addition. The reaction mixture was stirred at 70° to 75° C. for 20 minutes to one hour after the thionyl chloride addition was complete. The reaction mixture temperature was then gradually increased to 85° C. Ad kept at this temperature until solids began to form in the reaction mixture. This required approximately two hours at 85° C. Hydrogen chloride and sulfur dioxide continued to evolve from the reaction mixture during both of these temperature holds. The reaction mixture temperature was gradually raised to 95° C. Ad held at this temperature until the gas evolution of hydrogen chloride and sulfur dioxide stopped. This required about two and one half hours at 95° C. The reaction mixture was then cooled to room temperature. The reaction mixture was filtered. The filter cake was washed with 1.63 parts toluene and dried in a vacuum desiccator at ambient temperature. The dry filter cake was a white, free-flowing, non-dusty powder. This material was determined to be 3-chloromethylpyridinium hydrochloride having a purity of about 98 weight percent. The yield was 99+%. Approximately 96 weight percent of the aggregates had an average diameter greater than 300 microns as measured by microscopy using automated image analysis.

EXAMPLE 2

A dry, four neck, round bottom flask was setup with an overhead stirrer, reflux condenser, rubber septum, and thermometer. The reaction set up was flushed with dry nitrogen and the following reaction was carried out under an atmosphere of dry nitrogen. The reaction flask was charged with one part 3-hydroxymethyl pyridine dissolved in 4.33 parts toluene. A glass tube was placed through the rubber septum on the reaction flask so that its opening was just above the surface of the stirred reaction mixture. Anhydrous hydrogen chloride was blown through this tube onto the surface of the stirred reaction mixture until no more hydrogen chloride was absorbed by the reaction mixture. A white precipitate formed during the hydrogen chloride addition. This precipitate was determined to be 3-hydroxymethyl pyridinium hydrochloride. This precipitate was recovered by filtration of the reaction mixture. The filter cake was dried under vacuum at room temperature.

Five reaction flasks were setup. Each reaction flask was equipped with an overhead stirrer, reflux condenser, addition funnel, and thermometer. The first reaction flask was charged with 26.7 parts of the above 3-hydroxymethyl pyridinium hydrochloride and 86.7 parts of toluene. The second flask was charged with 20 pads 3-hydroxymethyl pyridinium hydrochloride, five parts 3-hydroxymethyl pyridine, and 86.7 parts toluene. The third flask was charged with 13.34 parts 3-hydroxymethyl pyridinium hydrochloride, 10 parts 3-hydroxymethyl pyridine, and 86.7 parts toluene. The fourth flask was charged with 6.7 parts 3-hydroxymethyl pyridinium hydrochloride, 15 parts 3-hydroxymethyl pyridine, and 86.7 parts toluene. The fifth flask was charged with 20 parts 3-hydroxymethyl pyridine, and 86.7 parts toluene. Twenty four parts of thionyl chloride was added dropwise to each of the five reaction mixtures under agitation. Each of these reaction mixtures was stirred and heated between 70° and 85° C. until gas evolution ceased. Each reaction mixture was cooled to room temperature and filtered. Each filter cake was washed with toluene and dried at room temperature under vacuum. The crude yield from each of these reactions was greater than 99%.

Samples from each of these five reaction mixtures were assayed by titrimetry in acetone using tetra-n-butylammonium hydroxide as titrant and following the assay method described herein. The assay results appear in Table 1.

TABLE 1

| FLASK # | 1 | 2 | 3 | 4 | 5 |
|---|---|---|---|---|---|
| Molar Equivalents[1] of Hydroxymethyl pyridinium Hydrochloride in solution or dispersion | 100% | 75% | 50% | 25% | 0% |
| Initial Molar Equivalents[2] of HCl gas used to prepare solution or dispersion | 1.0 | .75 | .5 | .25 | 0 |
| Purity (weight percent) | 98% | 98% | 98% | 96% | 88% |
| Yield (weight percent) | 99 | 99 | 99 | 99 | 99 |
| Color | white | white | light yellow | light yellow | yellow |
| Non-Dusting | YES | YES | YES | YES | YES |

[1]Based on the total molar equivalents of hydroxymethyl pyridinium hydrochloride and any hydroxymethyl pyridine in the solution or dispersion.
[2]Based on the initial number of hydroxymethyl pyridine equivalents used to prepare the solution or dispersion.

EXAMPLE 3

A dry, four neck, round bottom flask was set up with an overhead stirrer, reflux condenser, rubber septum, and thermometer. The reaction setup was flushed with dry nitrogen and the following reaction was carried out under an atmosphere of dry nitrogen. The reaction flask was charged with 20 parts 3-hydroxymethyl pyridine and 68.4 parts n-heptane. The reaction mixture was two immiscible liquid phases. A glass tube was placed through the rubber septum on the reaction flask so that its opening was just above the surface of the stirred reaction mixture. Anhydrous hydrogen chloride was blown through this tube onto the surface of the stirred reaction mixture until 6.7 parts hydrogen chloride was absorbed by the reaction mixture. A white precipitate formed during the hydrogen chloride addition. This precipitate formed clumps on the walls of the reaction flask. The rubber septum and glass tube were removed from the reaction flask and replaced with an addition funnel. The addition funnel was charged with 24 parts thionyl chloride. The thionyl chloride was added dropwise to the stirred reaction mixture. The reaction mixture temperature was maintained between 75° and 85° C. during this addition and kept at this temperature until gas evolution stopped. The reaction mixture was cooled to room temperature. A white solid was scraped from the walls of the reaction flask. The solvent was removed from these solids by filtration. The filtered solids were washed with n-heptane and dried at room temperature under vacuum. The yield was 99+%. The purity was about 96%

EXAMPLE 4

A dry, four neck, round bottom flask was setup with an overhead stirrer, reflux condenser, rubber septum, and thermometer. The reaction setup was flushed with dry nitrogen and the following reaction was carried out under an atmosphere of dry nitrogen. The reaction flask was charged with 20 parts 3-hydroxymethyl pyridine and 77 parts methylcyclohexane. The reaction mixture was two immiscible liquid phases. A glass tube was placed through the rubber septum on the reaction flask so that its opening was just above the surface of the stirred reaction mixture. Anhydrous hydrogen chloride was blown through this tube onto the surface of the stirred reaction mixture until 6.7 parts hydrogen chloride was absorbed by the reaction mixture. A white precipitate formed during the hydrogen chloride addition. The rubber septum and glass tube were removed from the reaction flask and replaced with an addition funnel. The addition funnel was charged with 24 parts thionyl chloride. The thionyl chloride was added dropwise to the stirred reaction mixture. The reaction mixture was a white granular powder being stirred in solvent when gas evolution stopped. The reaction mixture was cooled to room temperature and filtered. The filtered solids were washed with methylcyclohexane and dried at room temperature under vacuum. A substantially dusting free white solid having a purity of about 99+% was produced in a yield of 99+%. Approximately 82% weight percent of the aggregates had an average diameter greater than 300 microns in size as measured by microscopy using automated image analysis. Using light microscopy, the product appeared as aggregates that were relatively pseudo cubic.

EXAMPLE 5

A dry, four neck, round bottom flask was setup with an overhead stirrer, reflux condenser, rubber septum, and thermometer. The reaction setup was flushed with dry nitrogen and the following reaction was carried out under an atmosphere of dry nitrogen. The reaction flask was charged with 20 parts 3-hydroxymethyl pyridine and 86 parts xylenes (a mixture of ortho, meta, and para xylene). The reaction mixture was two immiscible liquid phases. A glass tube was placed through the rubber septum on the reaction flask so that its opening was just above the surface of the stirred reaction mixture. Anhydrous hydrogen chloride was blown through this tube onto the surface of the stirred reaction mixture until 6.7 parts hydrogen chloride was absorbed by the reaction mixture. A white precipitate formed during the hydrogen chloride addition. The rubber septum and glass tube were removed from the reaction flask and replaced with an addition funnel. The addition funnel was charged with 24 parts thionyl chloride. The thionyl chloride was added dropwise to the stirred reaction mixture. The reaction mixture temperature was maintained between 75° and 85° C. during this addition and kept at this temperature until gas evolution stopped. The reaction mixture was cooled to room temperature and filtered. The filtered solids were washed with xylenes and dried at room temperature under vacuum. A substantially non-dusting white solid having a purity of about 97% was produced in a yield of 99+%.

EXAMPLE 6

A dry, four neck, round bottom flask was setup with an overhead stirrer, reflux condenser, rubber septum, and thermometer. The reaction setup was flushed with dry nitrogen and the following reaction was carried out under an atmosphere of dry nitrogen. The reaction flask was charged with 20 parts 3-hydroxymethyl pyridine and 86.4 parts mesitylene. The reaction mixture was two immiscible liquid phases. A glass tube was placed through the rubber septum on the reaction flask so that its opening was just above the surface of the stirred reaction mixture. Anhydrous hydrogen chloride was blown through this tube onto the surface of the stirred reaction mixture until 6.7 parts hydrogen chloride was absorbed by the reaction mixture. A white precipitate formed during the hydrogen chloride addition. The rubber septum and glass tube were removed from the reaction flask and replaced with an addition funnel. The addition funnel was charged with 24 parts thionyl chloride. The thionyl chloride was added dropwise to the stirred reaction mixture. The reaction mixture temperature was maintained between 75° and 85° C. during this addition and kept at this temperature until gas evolution stopped. The reaction mixture was cooled to room temperature and filtered. The filtered solids were washed with mesitylene and dried at room temperature under vacuum. A substantially non-dusting white solid having a purity of about 97% was produced in a yield of 99+%.

EXAMPLE 7

The procedure described in Mosher et al. in the *Journal of the American Chemical Society*, vol. 73, pp 4925–4927, (1951) was reproduced to produce 3-chloromethylpyridine.

A dry, four neck, one liter, round bottom flask was set up with an overhead stirrer, reflux condenser, and thermometer. The fourth neck of the reaction flask was closed with a glass stopper. The exit from the condenser was vented to a caustic scrubber. The reaction setup was flushed with dry nitrogen and the following reaction performed under a nitrogen atmosphere. The reaction flask was charged with 150 ml of thionyl chloride. The stopper on the reaction flask was replaced with a powder funnel and 37.1 g of 3-hydroxymethyl pyridinium hydrochloride added to the stirred reaction mixture. The powder funnel was removed and the stopper replaced. The stirred reaction mixture was gently warmed with a heat gun to 70° C. After the initial vigorous reaction had subsided, a heating mantle was placed on the reaction flask and the stirred reaction mixture heated to reflux for two hours. The heating mantle was removed and the reaction mixture allowed to cooled to room temperature. The stirred reaction mixture was diluted with 250 mL of benzene. The white solid which precipitated was collected by vacuum filtration with a sintered glass funnel. The filter cake was washed with benzene and dried at room temperature in a vacuum desiccator. The dry, white product mixture had a weight of 38.0 g. The yield was 91%. The purity was 99% using the titrametric assay method described above. Approximately 4 weight percent of the crystals or particles were greater than 300 microns in size as measured by microscopy using automated image analysis. Viewed using light microscopy, the product appeared as needle to tabular shaped crystals, most of which were not aggregrates. The material was dusting in character.

EXAMPLE 8

A dry, four neck, round bottom flask was setup with an overhead stirrer, reflux condenser, rubber septum, and thermometer. The reaction setup was flushed with dry nitrogen and the following reaction was carried out under an atmosphere of dry nitrogen. The reaction flask was charged with 20 parts 3-hydroxymethyl pyridine and 70.3 parts n-octane. The reaction mixture was two immiscible liquid phases. A glass tube was placed through the rubber septum on the reaction flask so that its opening was just above the surface of the stirred reaction mixture. Anhydrous hydrogen chloride was blown through this tube onto the surface of the stirred reaction mixture until 6.7 parts hydrogen chloride was absorbed by the reaction mixture. A white precipitate formed during the hydrogen chloride addition. The rubber septum and glass tube were removed from the reaction flask and replaced with an addition funnel. The addition funnel was charged with 24 parts thionyl chloride. The thionyl chloride was added dropwise to the stirred reaction mixture. The reaction mixture temperature was maintained between 75° and 85° C. during this addition and kept at this temperature until gas evolution stopped. The reaction mixture was cooled to room temperature and filtered. The filtered solids were washed with n-octane and dried at room temperature under vacuum. A substantially non-dusting white solid having a purity of about 97% was produced in a yield of 99+%.

Although the present invention has been described with reference to certain preferred embodiments, it is apparent that modification and variations thereof may be made by those skilled in the art without departing from the scope of this invention as devined by the appended claims.

We claim:

1. A process for the preparation of chloroalkyl pyridinium hydrochloride compounds comprising the steps of:
  a) generating a solution or a dispersion comprising a hydroxyalkyl pyridinium hydrochloride compound in a medium comprising at least one non-solvent for the chloroalkyl pyridinium hydrochloride;
  b) admixing thionyl chloride with said solution or dispersion generated in step (a) to form a reaction mixture;
  c) reacting the thionyl chloride with the hydroxyalkyl pyridinium hydrochloride to form the chloroalkyl pyridinium hydrochloride, at least a portion of which forms as a solid in the reaction mixture.

2. A process according to claim 1 wherein the hydroxyalkyl pyridinium hydrochloride compound has the general formula:

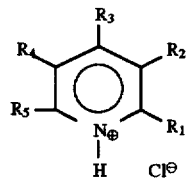

wherein
  $R_1$ through $R_5$ are substituents independently selected from the group consisting of:
  hydrogen, halogen, a hydrocarbyl group having 1 to 30 carbons, a halo substituted hydrocarbyl group having 1 to 30 carbons and any two of $R_1$ through $R_5$ together form a ring selected from the group consisting of aromatic, cycloalkane and heterocyclic rings; provided that at least one of $R_1$ through $R_5$ is a hydroxyalkyl group.

3. A process according to claim 1 wherein said solution or dispersion in step (a) is generated by reacting a hydroxyalkyl pyridine compound with at least about 0.25 equivalents of hydrogen chloride and/or hydrochloric acid, based on the number of basic heteroaromatic equivalents in a medium comprising at least one non-solvent for the chloroalkyl pyridinium hydrochloride.

4. A process according to claim 3 wherein the hydroxyalkyl pyridine compound has the general formula:

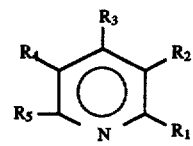

wherein
  $R_1$ through $R_5$ are substituents independently selected from the group consisting of:
  hydrogen, halogen, a hydrocarbyl group having 1 to 30 carbons, a halo substituted hydrocarbyl group having 1 to 30 carbons; and any two of $R_1$ through $R_5$ together form a ring selected from the group consisting of aromatic, cycloalkane and heterocyclic rings; provided that at least one of $R_1$ through $R_5$ is a hydroxyalkyl group.

5. A process for the preparation of 3-chloromethyl pyridinium hydrochloride which comprises the steps of:
  a) generating a solution or a dispersion comprising 3-hydroxymethyl pyridinium hydrochloride in a medium comprising at least one non-solvent for 3-chloromethyl pyridinium hydrochloride;
  b) admixing thionyl chloride with said solution or dispersion generated in step (a) to generate a reaction mixture; and
  c) reacting thionyl chloride with 3-hydroxymethyl pyridinium hydrochloride to form 3-chloromethyl pyridinium hydrochloride, at least a portion of which forms as a solid in the reaction mixture.

6. A process according to claim 5 wherein said solution or dispersion in step (a) is generated by reacting 3-hydroxymethyl pyridine with at least about 0.25 equivalents of hydrogen chloride and/or hydrochloric acid, based on the number of basic heteroaromatic equivalents, in a medium comprising at least one non-solvent for the chloromethyl pyridinium hydrochloride.

7. A process according to claim 5 wherein at least about 1 equivalent of hydrogen chloride or hydrochloric acid based on the number of basic heteroaromatic equivalents, is reacted with 3-hydroxymethyl pyridine.

8. A process according to claim 5 wherein the solution or dispersion additionally comprises 3-hydroxymethyl pyridine and the molar equivalent amount of 3-hydroxymethyl pyridinium hydrochloride in the solution or dispersion is at least about 25%, based on the total molar equivalents of 3-hydroxymethyl pyridinium hydrochloride and 3-hydroxymethyl pyridine in the solution or dispersion.

9. A process according to claim 5 wherein the non-solvent is selected from the group consisting of toluene, xylenes, mesitylene, methyl cyclohexane, benzene, hexanes, heptanes, cyclohexane, octanes and mixtures thereof.

10. A process according to claim 5 wherein the non-solvent is a hydrocarbon which will produce chloroalkyl pyridinium hydrochloride in substantially non-dusting form.

11. A process according to claim 5 wherein the nonsolvent is toluene or a mixture of toluene and a hydrocarbon.

12. A process according to claim 5 wherein said solution or dispersion in step (a) is maintained at a temperature ranging from about 70° C. to about 79° C. prior to admixing thionyl chloride to said solution or dispersion.

13. A process according to claim 5 wherein the amount of thionyl chloride admixed with the solution or dispersion in step (a) is about a 200 equivalent percent excess or less, based on the number of hydroxy equivalents of 3-hydroxymethyl pyridinium hydrochloride and any 3-hydroxymethyl pyridine compound in the solution or dispersion.

14. A process according to claim 5 wherein the amount of thionyl chloride admixed with the solution or dispersion in step (a) ranges from about 1 equivalent to about 10 equivalent percent excess, based on the number of hydroxy equivalents of 3-hydroxymethyl pyridinium hydrochloride and any 3-hydroxymethyl pyridine compound in the solution or dispersion.

15. A process according to claim 5 wherein the thionyl chloride and 3-hydroxymethyl pyridinium hydrochloride are reacted at a temperature not exceeding the boiling point of the reaction mixture.

16. A process according to claim 5 wherein after thionyl chloride begins to react with 3-hydroxymethyl pyridinium hydrochloride, the reaction mixture is heated to a temperature and for a time sufficient for at least a portion of 3-chloromethyl pyridinium hydrochloride to form as a solid in the reaction mixture.

17. A process according to claim 16 wherein said temperature ranges from about 75° C. to about 90° C. Ad said temperature is maintained within said range for a period of time ranging from about 0.5 to about 10 hours.

18. A process according to claim 5 wherein after a portion of the 3-chloromethyl pyridinium hydrochloride forms as a solid in the reaction mixture, the reaction mixture is heated to a temperature sufficient to drive the reaction in step c) to completion.

19. A process according to claim 18 wherein said temperature ranges from about 90° to about 100° C. Ad said temperature is maintained within said range for a period of time ranging from about 3 minutes to about 6 hours.

20. A process according to claim 5 wherein the 3-chloromethyl pyridinium hydrochloride compound is recovered.

21. A process according to claim 20 wherein the yield of 3-chloromethyl pyridinium hydrochloride recovered is at least about 97 percent.

22. A process for the preparation of substantially pure, substantially non-dusting 3-chloromethyl pyridinium hydrochloride comprising the steps of:

a) generating a solution or dispersion comprising 3-hydroxymethyl pyridinium hydrochloride in a medium comprising toluene, by reacting in said medium, 3-hydroxymethyl pyridine with at least about 1 equivalent of hydrogen chloride, based on the number of pyridine nitrogen equivalents;

b) admixing thionyl chloride with said solution or dispersion generated in step (a) to form a reaction mixture;

c) heating the reaction mixture to a temperature ranging from about 75° C. to about 90° C. for a period of time ranging from about 0.5 to about 10 hours;

d) heating the reaction mixture to a second temperature ranging from about 90° C. to about 100° C. Ad maintaining said second temperature within said range for a period of time of from about 3 minutes to about 6 hours; and e) recovering 3-chloromethyl pyridinium hydrochloride from the reaction mixture in a substantially high yield.

23. A process according to claim 22 wherein the 3-chloromethyl pyridinium hydrochloride compound is recovered in a yield of at least 98 weight percent.

* * * * *